United States Patent [19]

Lauterjung

[11] 4,236,521
[45] Dec. 2, 1980

[54] PROBE

[76] Inventor: Friedrich G. Lauterjung, Schallstrasse 6, 5000 Cologne 41, Fed. Rep. of Germany

[21] Appl. No.: 902,373

[22] Filed: May 3, 1978

[30] Foreign Application Priority Data

May 13, 1977 [DE] Fed. Rep. of Germany ....... 2721548

[51] Int. Cl.³ .............................................. A61M 25/00
[52] U.S. Cl. ..................................... 128/348; 128/222
[58] Field of Search ............................... 128/348–351, 128/344, 638, 768, 780, 401, 222

[56] References Cited

U.S. PATENT DOCUMENTS

| 3,811,450 | 5/1974 | Lord | 128/349 B X |
| 4,085,757 | 4/1978 | Pevsner | 128/348 X |

FOREIGN PATENT DOCUMENTS 2402573  7/1975  Fed. Rep. of Germany ........... 128/348

Primary Examiner—Dalton L. Truluck
Attorney, Agent, or Firm—Martin A. Farber

[57] ABSTRACT

A probe, particularly for enteral feeding of living creatures, with a balloon coordinated to the insertion end of the probe tube, the balloon being fillable with liquid and emptiable in the inserted condition. The probe tube end is secured on a pilot probe and is detachable from the outside.

18 Claims, 10 Drawing Figures

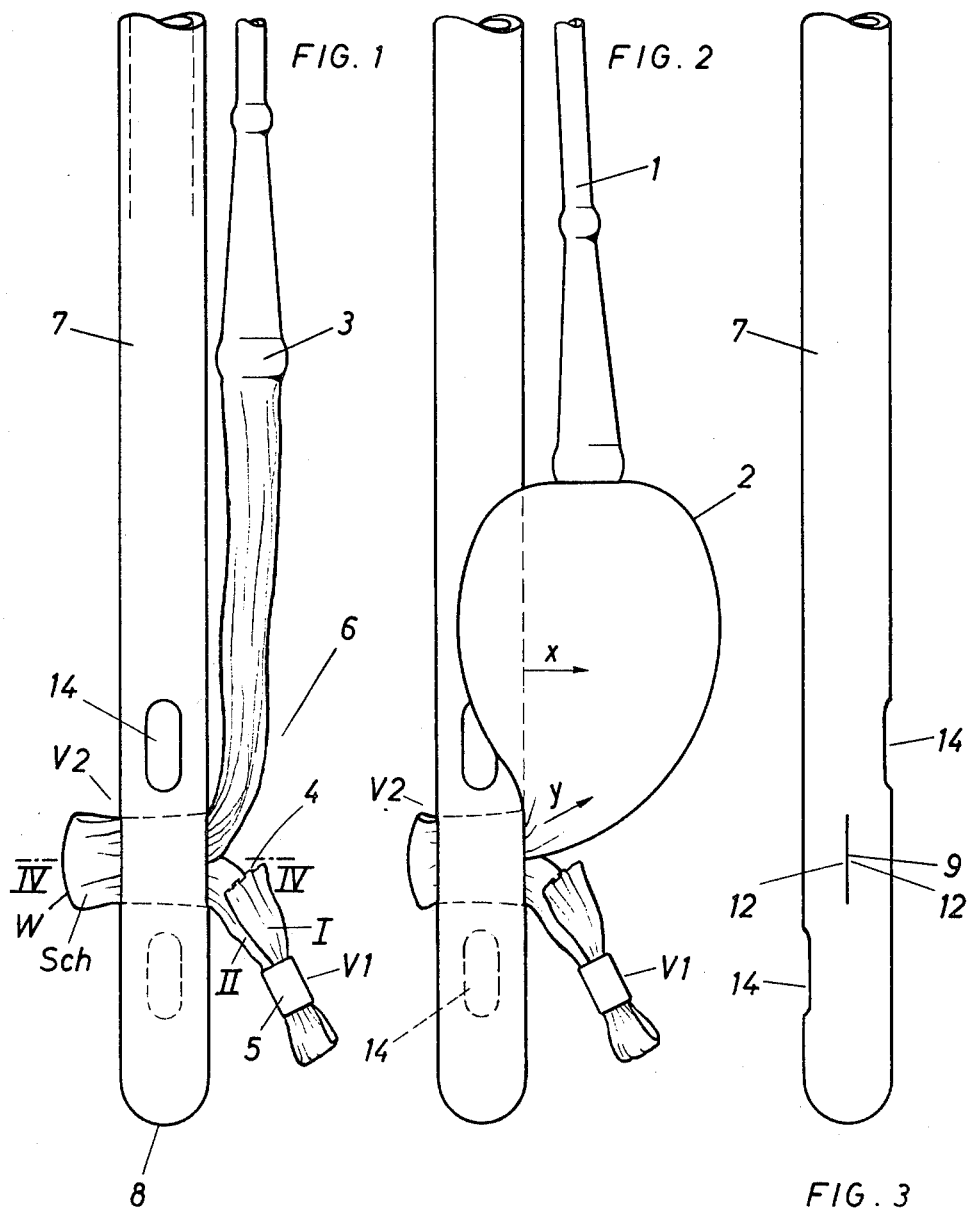
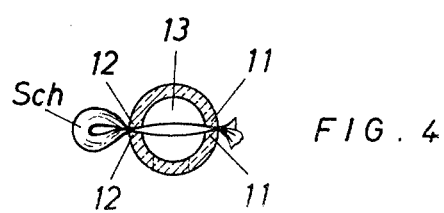

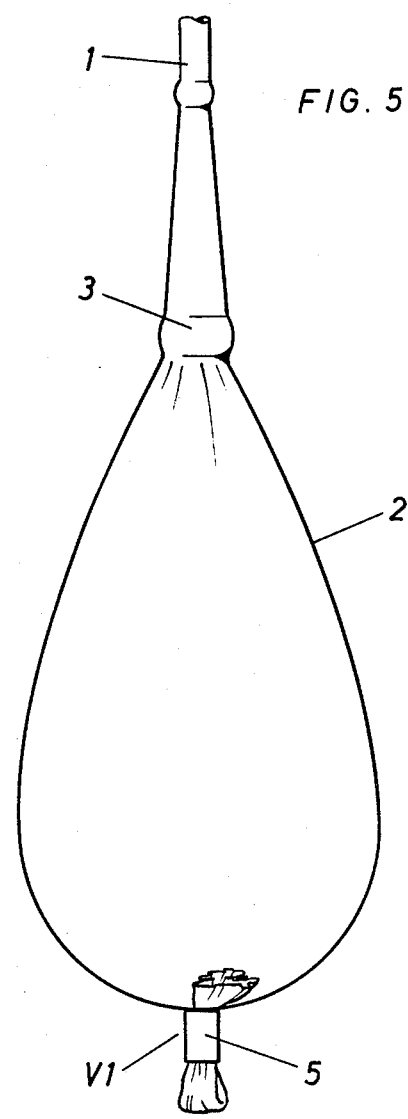
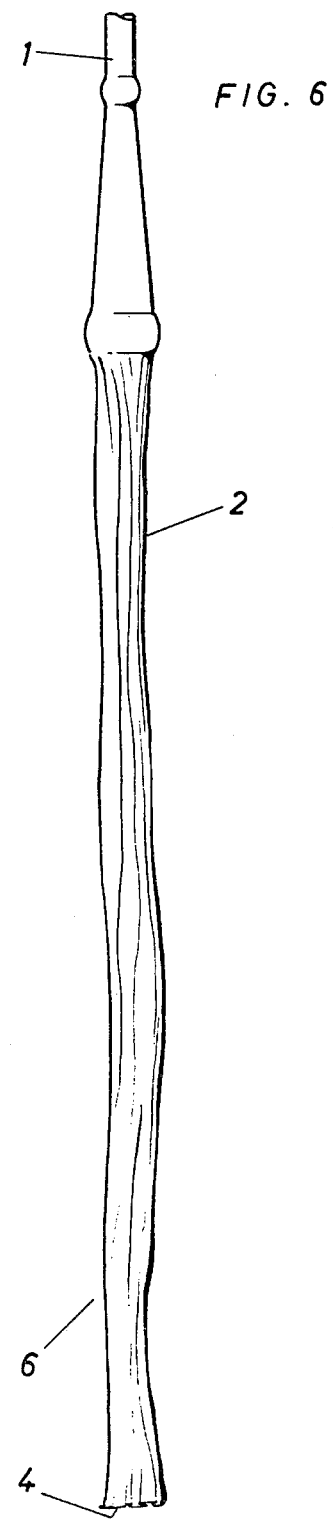

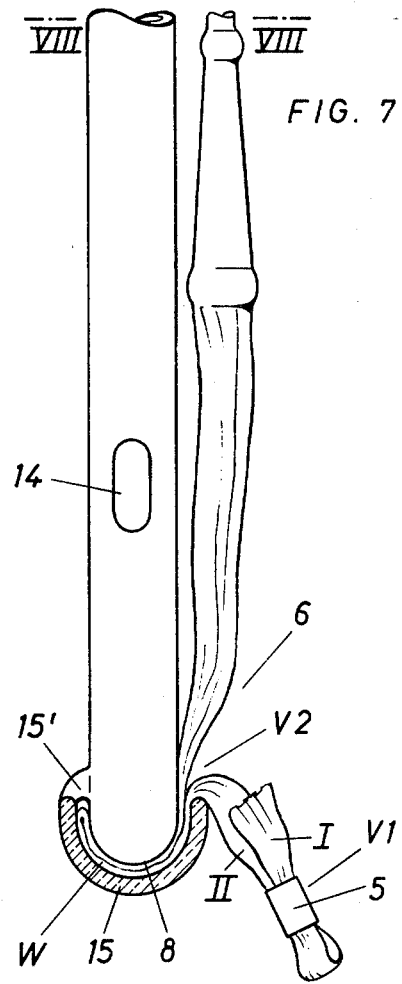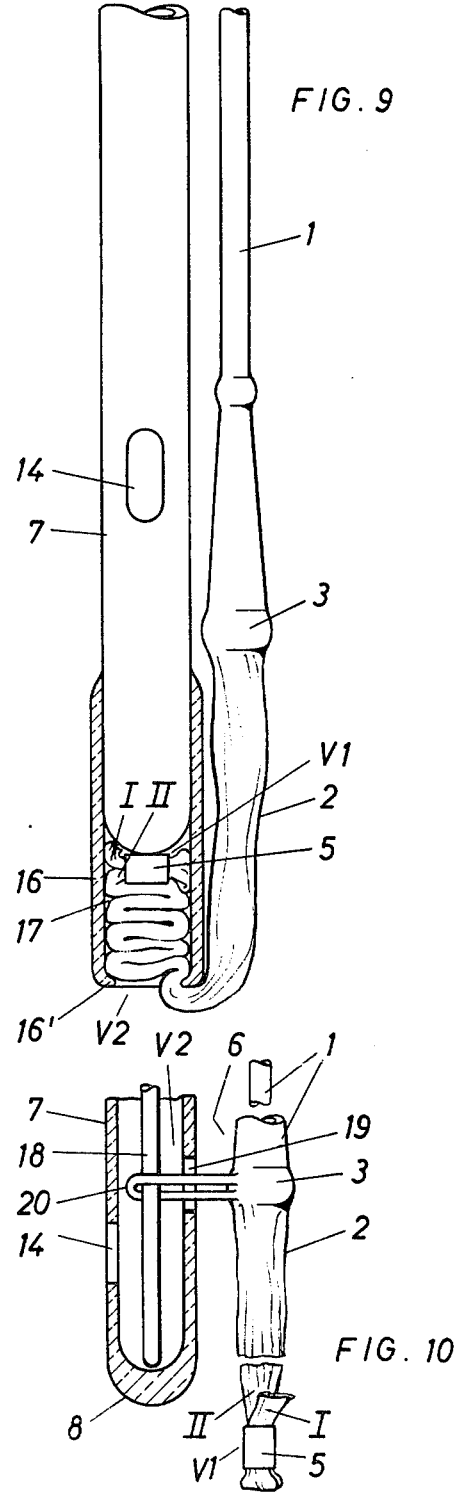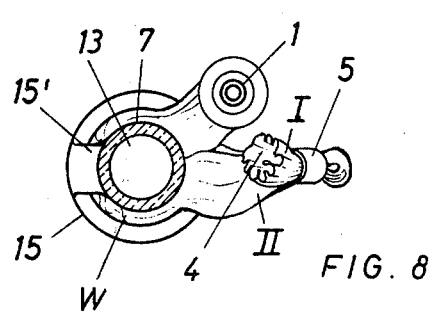

PROBE

The invention relates to a probe, particularly for enteral feeding of living creatures, by which a balloon is coordinated to the insertion end of the probe tube, which balloon is fillable with liquid and is emptiable in the inserted condition.

Corresponding alimentary probes serving the administration of liquid nutrient in stomachs or for example the duodenum may be formed with a most extremely small caliber, an outer diameter of the probe tube under 2 mm being usual. The transfer to the target site takes place with the use of a guide weight in the form of a liquid substance which enters the balloon which lies on the insertion side. Known intestinal probes make possible the detaching of the guide weight, which can then leave the target site in a natural manner. The use of such probes is however not possible with constrictions in the intestinal tract, since under circumstances it can produce an intestinal obstruction. With the latter its use is completely impossible.

Although cross-sectionally small probes actually projecting from patients normally, with respect to the introduction as well as the long period of lying in bed, are tolerated, thus the introduction in patients with poor general condition and their consequently dependent passivity are mostly still difficult after all, particularly with fainting conditions.

The object of the invention particularly is to form such a probe of advantageous use in a simpler technical manner of production, such that the insertion section having little windings is quickly and surely overcome also without activity on the part of the patients, so that upon reaching the winding multiple zones, the actual target site then is reached with the use of the filling weight and regulatable balloon cross-section, respectively, and the natural peristalsis.

In the modern ileus treatment, for a long time two lumen probes are used (Münchener Medizinische Wochenschrift 110/1968, pages 470-474), which carry in the medicine section the designation Miller-Abbott probe. Here the filling weight indeed is pulled off over an integrated second line of the probe tube, whereas the other line or chamber communicates with the stomach or intestinal space. This tube is however relatively thick in cross section and thus rigid so that here first of all the problem of the coordination compatibility or tolerance exists. It also can not be brought to any desired target site and already on this basis it is unsuited as a nutrient or alimentary probe. Correspondingly thick probe tubes in addition can not lie for a long time in the patient.

The invention to the contrary provides the use of a probe part which makes possible an active insertion only for a limited insertion path and accordingly a limited time duration. A probe of this type thus fulfills only a pilot function. It drags the substantially cross-sectionally smaller probe tube which is fastened on its tip safely into the selected exit or starting range. The pilot probe is then disconnected and removed from the inserted probe tube end. This disconnection takes place from the outside and indeed with the use of a partial filling up of the balloon, which under increasing filling pressure "pushes itself off" from the pilot probe. Concerning this it is advantageous when the balloon, with the use of a clamping connection between the pilot probe and the probe tube, is coupled with the latter. The flexibility of the material from which the probe is made, can thereby most favorably be used for achieving an elastic clamping connection, for example, advantageously in the manner that the balloon wall is clamped or squeezed in a slot of the pilot probe. A corresponding slot may be formed during probe manufacturing with a contemplated probe, or still also may be provided anytime on an existing probe, for example, a conventional stomach probe, by providing a corresponding cut. Since a pilot probe used of this form, by its tube formation indeed then can have two slots arranged in diametrically opposite position, practically two clamping zones independent from one another are made, so that the coordination security which is aimed at exists in spite of the decoupling which surely can be carried out.

After the exact placement, the liquid can be supplied which forms the guide weight as well as the enlarged carrier cross-section, which takes place in the manner of the remaining filling of the balloon at the end side, which balloon is closeable by a removable closure member. Such a closure member can be realized in the form of a nominal or desired breaking zone in the balloon wall, or in a likewise favorable manner also by a strippable collar of the balloon, the latter having an end opening, which collar is slipped on a folded loop. This collar holds together the two balloon wall sections that are laid correspondingly against each other, i.e. bent balloon wall sections, until the moment of the increase of the inner pressure in the balloon. The preconnection of a clamping zone with security brings about a timewise succession of detaching and opening. The partial filling up alone consequently does not cause the opening of the tube. On the other hand by pulling off the filling weight, a cross-section reduction of the balloon can take place in adjustment or adaptation to given necessities, for example with mechanical obstacles. After opening of the balloon, the supply of the nutrient liquid can be started. The emptied, now slack ballon body joins or follows as a tube zone extending the probe, which zone steps back cross-sectionalwise indeed still behind those of the cross-section of the probes, and as a result of the extremely small wall thickness has a still greater readiness to adjust to the winding courses. Another favorable form of the construction of a coupling/clamping connection resides in the coordination of a terminal clamping cap for the clamping of the balloon wall. This cap is blasted off during partial filling, however it remains on the pilot probe body and is again removed together with the latter. Another favorable solution is that the pilot probe on its end possesses a plug-in space for reception of a part of the balloon. The balloon which is predetermined for the insertion of the probe in sufficient measure, which balloon is folded-in for example in narrow bends, is lead out during partial filling, winding for winding, from this reception space, so that also here a safe decoupling of the probe tube end from the pilot probe is provided. A correspondingly high security of use is also provided by the measure that the pilot probe contains a pulling member for releasing the coupling connection, which pulling member extends up to the free end of the pilot probe. Here in an advantageous manner the pilot probe tube cavity is used for the accommodation of the pulling member. The end side connection mechanisms here can be embodied such that a loop originating from the balloon body projects into the range of the pulling member, which loop with corresponding withdrawal of the pulling member releases the balloon. On the other hand also still the balloon body itself, with formation of a loop, can be coordinated to the pilot probe such that the pulling member retains the bend or loop of this balloon, gripping behind the loop in a corresponding manner. The pilot probe can still also be arranged inside of the probe tube, for example formed such that the pulling member which serves for the decoupling constitutes the pilot probe. Here it can deal with a steel wire.

Further advantages and particulars of the subject matter of the invention are closely described in the following on the basis of several drawings of illustrative embodiment examples.

FIG. 1 is the probe according to the first embodiment example with illustration of the coupling/clamping connection, FIG. 2 is this probe with initiated release of the probe tube end from the pilot probe, FIG. 3 is a side view of the pilot probe in individual illustration with illustration of the clamping slot, FIG. 4 is a section according to the lines IV—IV in FIG. 1, FIG. 5 is the probe with the balloon partial filling forming the guide weight, which probe is released from the pilot probe, FIG. 6 is the balloon in the emptied condition, FIG. 7 is the probe according to a second embodiment example, with the clamping cap as the coupling/clamping connection means between the pilot probe and the probe tube illustrated in section, FIG. 8 is a section according to the lines VIII—VIII in FIG. 7, FIG. 9 is the probe according to the third embodiment example, according to which the balloon is accommodated in a reception space of the pilot probe and FIG. 10 is the fourth embodiment example of the probe with utilization of a pulling member as the actuating means neutralizing the coupling connection.

The alimentary probe comprises a flexible tube 1, the distal end of which continues in a balloon 2 which is equally attached, or separately coordinated, however then not removeable. The latter is formed by an extremely thin walled tubular body originating from an end side tube bead 3. Its open end 4 is closed by a closure member 5. The latter is formed in the shape of a collar. For closing the end of the balloon, this collar is slipped on the correspondingly balloon wall sections I and II which are folded against one another from the fold bend end, so that it holds together the folded-over sections forming the closure position VI which is achieved by bending.

The closing location VI lies on the other side of a connection location V2 between the probe end 6 (which end is formed by the balloon 2) and a pilot probe 7. The latter is relatively stiff relative to the probe 1 and is formed substantially larger in cross-section, such that it is actively insertable while carrying along the probe tube 1, the latter being fastened on its insert side end. Its end 8 has a dome-shaped form.

At any time and thus also in the inserted condition, the probe tube 1 is detachable from outside of the pilot probe 7. For this purpose a clamping connection is used. The pilot probe 7, for that purpose, in the end range has a small longitudinal slot (stick-in space) 9. A loop Sch of the balloon wall W is pulled in the longitudinal slot. For separating the probe tube end from the pilot probe 7, a filling medium is introduced from the free probe tube end, preferably in the form of a liquid substance forming the filling weight, and indeed at first only as a partial filling. The probe tube sided end section of the balloon 2 in this case enlarging in cross-section, pushes the probe end off from the pilot probe 7 (arrow x) and thereby pulls out the loop Sch (which loop clamps off the remaining space) from the longitudinal slot 9 (arrow y), (the latter slot forming the coupling/clamping), so that in the end state by the filling pressure a complete separation of the pilot probe 7 and the probe tube 1 is brought about. The pilot probe thereafter can be pulled off.

By further filling, now the balloon which forms the guide weight is brought to the desired cross-section so that with utilization of the peristalsis the tube migrates to the target site. Upon reaching the same, the balloon 2 is opened by means of finishing the filling. The collar-like closure member 5 which is set or matched to a predetermined filling pressure, is pushed down from the balloon wall sections I and II (which sections are folded on one another forming the closure position VI), so that the balloon contents flow off and the supply of the nutrient liquid can be started.

The connection location (or clamp fastening location) V2 is placed such that approximately half of the tube which forms the balloon stands available for the partial filling. The remaining length is used for the formation of the loop Sch and for formation of the end side closure position VI.

The slot 9 forms with a tubular shaped pilot probe, two clamping lip pairs 11 and 12, respectively, which are diametrical opposite each other. Corresponding to the longitudinal alignment of the slot 9, the held section of the balloon is set through the probe cavity 13 as a narrow stay, so that an evacuation or sucking off of the stomach contents via the wall openings 14, which sucking off is perhaps necessary during insertion, is not hindered over the pilot probe then serving as a stomach probe. In lips formed of a tube wall, a particularly elastic clamping connection is brought between the pilot probe 7 and the probe tube 1.

The probe according to the second embodiment example differs from the previously described, in so far as, there the connection position V2 is formed from a clamping cap 15. This cap, corresponding to the dome-shape, extends from an articulation or hinge position 15' of the pilot probe and is pressed on with clamping of that section of the balloon wall W which is to be clamped. The terminal clamping cap 15 causes no enlargement of the pilot probe tip worth mentioning and can be coordinated to the latter attached, welded or also in the manner of an adhesive connection. The end section which hangs over the edge of the cap comprising the balloon wall sections I and II, moreover is closed by the strippable collar in the above described manner. The embodiment example according to FIG. 9 differs in so far from the rest in that here the pilot probe 7, on its introduction-sided end, forms a plug-in space 17, which space is formed by a slipped-on or attached sleeve 16. This space receives the end side half of the balloon 2, and indeed with formation of the fold layers indicated in FIG. 9, the last two of which form the closure position VI of the balloon (balloon wall sections I and II).

The fold layers are prevented from slipping out from the space 17 by an inwardly directed annular shoulder 16' of the sleeve on the exit side.

The embodiment example according to FIG. 10 again provides a modified pilot probe 7, in so far as this has a pulling member 18 extending up to its end in the form of a synthetic or plastic wire or steel wire, and indeed for releasing of the coupling connection between the pilot probe 7 and the probe tube 1. The pulling member 18 is stored or inserted in the pilot probe tube and set through a loop 20 in a lock-bolt manner, which loop extends through an opening 19 of the pilot probe wall. This loop can be attached directly or can be realized by a loop substantially in the type of the loop Sch in FIG. 1. After reaching of the desired exit point, the pulling member is displaced in the direction of the outside end of the probe so that the loop 20 is free and exits from the opening 19. The pilot probe hereafter is removeable. The reference characters are carried over analogously.

A further embodiment example resides in that the pilot probe is arranged inside of the probe tube 1 possibly in the shape of a sufficiently stiff steel core or bore. Also another material pairing is thinkable when this possesses the necessary slidability with respect to one another. The tube is made of synthetic or plastic material. As the pilot probe, for example, also the pulling member 18 which serves the decoupling can be used.

I claim:

1. A probe means, particularly for enteral feeding of living creatures extending from the outside in an inserted condition in the creatures, comprising
   a hollow probe tube defining an insertion end,
   a balloon constituting an end portion of said probe tube being coordinated to said insertion end of said probe tube and communicating therewith for filling the balloon, said balloon being adapted to be filled with liquid through said probe tube,
   a separate pilot probe along said probe tube constituting exclusively means for initially inserting said balloon in a push-in path and said insertion end of said probe tube partially into the living creature,
   means for emptying said balloon in an inserted condition detached completely from said pilot probe,
   said pilot probe extending up to said end portion of said probe tube, grasping said balloon at a portion other than an end of said balloon, said pilot probe non-fluidly communicating with said balloon, and being completely separable from said balloon, said pilot probe further being removable from the living creature without said balloon, the latter remaining in communication with the outside via said probe tube.

2. The probe means according to claim 1 wherein said pilot probe is formed with a stick-in space,
   said balloon has a balloon wall,
   a loop formed by said balloon wall is clamped in said stick-in space of said pilot probe, said stick-in space of said pilot probe defines a clamp fastening location on said balloon disposed at approximately half the length of the balloon.

3. The probe means as set forth in claim 2, wherein said stick-in space is formed as a slot in said pilot probe,
   said loop is clamped in the slot.

4. The probe means as set forth in claim 3, wherein said slot extends completely through said pilot probe and said balloon wall extends through said slot such that said loop extends outside said pilot probe.

5. The probe means according to claim 1, wherein said balloon has a wall,
   said pilot probe has a terminal clamping cap means for clamping of said wall of said ballon and releasing said wall of said balloon upon a partial filling of said balloon.

6. The probe means according to claim 1, wherein said pilot probe defines an insertion side end formed with a plug-in space,
   a portion of said balloon is removeably disposed in said plug-in space.

7. The probe means according to claim 1, wherein said pilot probe is arranged inside of said probe tube.

8. The probe means as set forth in claim 1, wherein said pilot probe holds said balloon at a fastening location on one side of said pilot probe,
   said balloon has two balloon wall sections which are folded together lying on the opposite side of said pilot probe and said fastening location, and
   said emptying means includes a collar holding said two balloon wall sections folded together, said collar being slidable off said balloon wall sections by a predetermined inner filling pressure in said balloon.

9. The probe means as set forth in claim 1, wherein said pilot probe grasps said balloon in an unfilled condition thereof during insertion together of said pilot probe and said balloon.

10. The probe means as set forth in claim 1, wherein said probe tube including said insertion end has a substantially smaller cross-section than that of said pilot probe.

11. The probe means as set forth in claim 1, wherein said balloon is adapted for being transported to a target site in a filled condition thereof by peristalsis after the complete separation from said pilot probe,
    said emptying means includes,
    closure means for holding said balloon closed until a predetermined inner filling pressure occurs in said balloon at the target site.

12. The probe means as set forth in claim 11, wherein said end of said balloon is open.

13. The probe means as set forth in claim 1, wherein said pilot probe is formed as a hollow tube.

14. The probe means according to claim 13, wherein said pilot probe defines an insertion side end,
    a coupling connection of said probe tube to said pilot probe adjacent said insertion side end,
    pulling means for decoupling said coupling connection,
    said pulling means is contained in said pilot probe and extends therein up to said insertion side end.

15. A probe means, particularly for enteral feeding of living creatures extending from the outside in an inserted condition in the creatures, comprising
    a probe tube defining an insertion end,
    a pilot probe adjacent to said probe tube,
    a balloon constituting a probe tube end being coordinated to said insertion end of said probe tube, said balloon being adapted to be filled with liquid,
    means for emptying said balloon in an inserted condition,
    means for securing said probe tube end on said pilot probe detachable from the outside,
    said securing means defines a connection position on one side of said pilot probe,
    said balloon has balloon wall sections lying on the opposite side of said pilot probe and said connection position,
    said emptying means includes closure means for holding said balloon wall sections together, said closure means for removing from said balloon wall sections by a predetermined inner pressure in said balloon.

16. The probe means according to claim 15, wherein said closure means constitutes a collar means for stripping off from said balloon wall sections by said predetermined inner pressure in said balloon.

17. The probe means according to claim 16, wherein said collar means combines said balloon wall sections in a folded-over condition.

18. The probe means as set forth in claim 15, wherein said balloon has an open end at an end of one of said wall sections.

* * * * *